United States Patent
Rajan et al.

Patent Number: 5,660,170
Date of Patent: Aug. 26, 1997

[54] RESPIRATORY APPARATUS AND METHOD FOR DETERMINING AN OPTIMAL OPENING PRESSURE IN A LUNG SYSTEM

[75] Inventors: Govinda Rajan, Rochelle Park, N.J.; Burkhard Lachmann, Lindenstr. 47a, D261 23 Oldenburg; Stephan Böhm, Bergisch Gladbach, both of Germany

[73] Assignee: Burkhard Lachmann, Oldenburg, Germany

[21] Appl. No.: 651,717

[22] Filed: May 22, 1996

[30] Foreign Application Priority Data

Jun. 2, 1995 [SE] Sweden .................. 9502031

[51] Int. Cl.⁶ .................. A61M 16/00
[52] U.S. Cl. .................. 128/204.18
[58] Field of Search .................. 128/202.22, 204.18, 128/204.21, 204.23, 205.11, 205.23

[56] References Cited

U.S. PATENT DOCUMENTS

| | | | |
|---|---|---|---|
| 3,961,627 | 6/1976 | Ernst et al. | 128/204.23 |
| 4,841,974 | 6/1989 | Gumbrecht et al. | |
| 4,917,080 | 4/1990 | Bayerlein | |
| 5,225,063 | 7/1993 | Gumbrecht et al. | |
| 5,239,995 | 8/1993 | Estes et al. | 128/204.23 |
| 5,365,922 | 11/1994 | Raemer | 128/204.23 |
| 5,398,682 | 3/1995 | Lynn | 128/204.23 |

FOREIGN PATENT DOCUMENTS 0 671 180  9/1995  European Pat. Off. .

OTHER PUBLICATIONS

"Open Up The Lung And Keep The Lung Open," Lachmann, Intensive Care Medicine, vol. 18 (1992) pp. 319–321.

*Primary Examiner*—Vincent Millin
*Assistant Examiner*—Robert N. Wieland
*Attorney, Agent, or Firm*—Hill, Steadman & Simpson

[57] ABSTRACT

In an apparatus and method for determining an optimal opening pressure of a lung system a regulating unit delivers an inspiration pulse having an end pressure which is higher than the start pressure to the lung system. During the delivery of this inspiration pulse respiratory gas flow and pressure are measured by a measuring unit having a flow meter and a pressure gauge. The measured values are supplied to a control unit, in which measured flow and pressure are correlated and inflection points or regions in the flow-pressure-relation are identified. The highest pressure value related to an inflection point or region is defined as an interim opening pressure. By applying several different inspiration pulses, several interim opening pressures can be determined. An optimal opening pressure is found when a corresponding partial pressure of oxygen, measured in a blood gas analyzing unit, exceeds a predetermined threshold, or by selecting the interim opening pressure resulting in an optimal relation to the supplied volume of gas.

13 Claims, 3 Drawing Sheets

RESPIRATORY APPARATUS AND METHOD FOR DETERMINING AN OPTIMAL OPENING PRESSURE IN A LUNG SYSTEM

BACKGROUND OF THE INVENTION

1. Field of the Invention

The present invention relates to an arrangement for determining an optimal opening pressure in a lung system, of the type having a regulating unit for supplying a respiratory gas to the lung system, a measuring unit for measuring at least one respiratory gas parameter and a control unit for determining the opening pressure based on the measured parameter(s).

The present invention also relates to a method for determining an optimal opening pressure in a lung system.

2. Description of the Prior Art

In a healthy lung, air passes during inspiration through the airways and bronchi to the alveoli in the lungs. An exchange of gas occurs in the alveoli, whereby blood is oxygenated and carbon dioxide is simultaneously transferred to air in the alveoli. Gas containing carbon dioxide is extracted from the alveoli during expiration, permitting the entry of fresh air during the following inspiration. Since a healthy lung has a large compliance, i.e. a high flexibility, a relatively large volume of air can be inhaled in each breath without excessive increases in the pressure of air in the lungs.

As a result of injuries or disease, the function of the lung can be effected to such a degree that a life threatening condition could develop. For example the alveoli might collapse, thereby impairing or, worse, preventing the essential exchange of gas between air in the alveoli and blood in the minute capillaries of the lungs. The lungs can also have atelectatic regions which reduce the compliance so much that an insufficient volume of air is inhaled in each breath. Connection of the damaged lung to a ventilator/respirator may then be necessary to keep a patient alive until the damaged lung has healed. A ventilator/respirator can deliver a respiratory gas to the lungs with a pressure high enough to open the collapsed alveoli in order to provide a sufficient gas exchange. The necessity of a high pressure follows the Laplace Law, $P=2\gamma/r$, where P is pressure, $\gamma$ is surface tension and r is radius. A collapsed alveolus has a very small radius, whereas an open alveoli has a (relatively) large radius, thereby requiring a lower pressure to remain open or to be further inflated. In a healthy lung, the alveoli have a layer of natural surfactant. The natural surfactant has the ability of varying its surface tension, thereby for the healthy lung keeping even the minute alveoli open at fairly low pressures. In a pathological condition, such as ARDS (Acute Respiratory Distress Syndrome), however, the alveoli may be depleted of surfactant, resulting in a constant, high air-tissue surface tension in the alveoli. This, of course, makes it even more difficult to open the collapsed alveoli.

The importance of opening the lungs and keeping them open is further described in an article entitled "Open up the lung and keep the lung open" by B. Lachmann, Intensive Care Medicine (1992) 18:319–321. Air at a relatively high pressure must be supplied to the lungs in order to force the alveoli to open, whereas a much lower pressure is required to keep the alveoli open, once they have been opened properly. At the same time, the risk of lung trauma in forced respiration increases at higher pressures (barotrauma) and/or larger volumes of respiratory gas (volume trauma), especially if lung compliance is simultaneously poor. Another risk connected with excessive pressures is that the capillaries can be damaged by shear forces developing within the lung or can be compressed so that the blood cannot flow through the capillaries (over-distension), thereby also preventing a gas exchange. In the aforementioned article it is also noted that a sufficient partial pressure of oxygen $P_aO_2$ in the blood is a sign of the efficiency of gas exchange in the alveoli, i.e., a measure of the degree to which the lungs are open.

In published Swedish Application 501 560 a ventilator/respirator is described which can determine an opening pressure of a lung based on the relation between measured pressure values and volume values of a respiratory gas supplied to a patient. Basically the ventilator delivers a constant flow of respiratory gas during inspiration and the resulting calculated. As long as the alveoli are collapsed the pressure will increase rapidly whereas pressure in the lung is measured the volume only increases slowly. As the alveoli open, the volume entering the lungs will increase more rapidly in relation to the pressure. The opening pressure is then determined by identifying the point of inflection in the P-V curve where the increase in volume becomes more rapid.

Although this procedure provides an opening pressure which can be used for determining the further treatment of the -patient, it is lacking somewhat insensitivity for determining an optimal opening pressure. For instance, there may be further inflection points in the P-V curve, which inflection points are not immediately identifiable as such. Further it does not guarantee that all collapsed alveoli have been opened properly.

SUMMARY OF THE INVENTION

It is an object of the present invention to provide a method and an apparatus for identifying an optimal opening pressure of the lungs for use in a respiratory system wherein the opening pressure can be accurately determined with a minimum risk of damaging the patient's lungs.

The above object is achieved in accordance with the invention in a method and apparatus wherein the regulating unit delivers a predetermined inspiration pulse, having an end pressure which is higher than its start pressure, and the measurement (or measurements) for determining an optimum opening pressure are made during the delivery of this inspiration pulse.

Instead of applying a constant flow of respiratory gas to the lung system and measure the resulting volume and pressure, as in the above described Swedish Application 501 560, an inspiration pulse having a predetermined pressure morphology is delivered to the lung system. In particular, the predetermined inspiration pulse has an end pressure which is higher than the start pressure. This results in a much more controlled increase of pressure toward the lung system, which is more beneficial to the lung system, since the risk of sudden excessive pressures within the lungs is basically removed completely. It is also easier to correlate a controlled pressure variable to a measured respiratory parameter. Further, since it is the opening pressure that is sought, a suitable shape of the inspiration pulse can be selected for increasing the sensitivity of the determination of the optimal opening pressure. For instance, the inspiration pulse can be selected so that the pressure increases rapidly at the onset of the inspiration phase and slowly in the neighborhood of an expected optimal opening pressure. The resulting reaction in the measured respiratory gas parameter in this neighborhood can then be more thoroughly evaluated.

In one embodiment of the invention, an inspiration pulse having a pressure increase in linear pressure stages from the start pressure up to the end pressure is used. For example, an inspiration pulse having a duration of nine seconds is to be delivered and the optimal opening pressure is suspected to be around 40 cmH$_2$O. The inspiration pulse could then consist of a first linear pressure stage, which elevates the pressure from 0 to 30 cmH$_2$O in two seconds and a second linear pressure stage, which elevates the pressure from 30 cmH$_2$O to 50 cmH$_2$O in the remaining seven seconds. The second linear pressure stage will be flatter and since the optimal opening pressure for a completely collapsed lung was suspected to be in the region of 30–50 cmH$_2$O, the slow increase during the latter part of the inspiration pulse will enhance the possibility of obtaining the optimal opening pressure. Other pressure and timing values can, of course, be utilized, depending on the individual case. In particular, the number of pressure stages, and their respective duration and pressure, could be selected from a vast range of possibilities.

In another embodiment of the invention, the respiratory gas flow is measured by a flow meter in the measuring unit and the control unit determines the optimal opening pressure based on the measured respiratory gas flow. If a flow curve is recorded and correlated to the applied pressure, the flow curve will show inflection points or inflection regions where an increase in flow follows the opening of alveoli. The amount of alveoli opening is reflected in the size of the increase in the flow. In other words, if a major part of the alveoli open up at the same time, a large increase in flow will be noted, and if only a smaller number of alveoli open, the increase will be smaller. As the pressure increases during the inspiration pulse, several inflection regions can occur. This is due to the fact that all alveoli will not open simultaneously. Different sizes of the alveoli and different pressure distribution within different compartments of the lungs result in the effect that different areas of the lung open at different pressures. The flow, however, is a more sensible tool than, for instance, supplied volume. Even a small number of alveoli opening, will result in an identifiable change in the measured flow. The applied pressure can be obtained either directly from the regulating unit or by disposing a pressure gauge in or near the lung system for measuring the pressure on site.

It is advantageous to deliver a series of consecutive identical inspiration pulses and then calculate the average values for corresponding measured parameters. The response of the lung system will not change dramatically from one respiratory cycle to the next and the determining of the optimal opening pressure can thus be improved.

In yet another embodiment of the invention, the regulator unit delivers a sequence of such series. Each series can comprise a differently shaped inspiration pulse and the control unit can determine an interim opening pressure for each series. The optimal opening pressure can then be determined from the interim opening pressures. The optimum opening pressure can, for instance, be determined by relating the supplied gas volume to the interim opening pressure. For instance, the quotient obtained by dividing each interim opening pressure by the supplied gas volume in the interval from onset of the inspiration pulse up to the interim opening pressure could be minimized. In other words, as large a volume as possible should be supplied at a pressure which is as low as possible.

In connection with this embodiment, it is advantageous to use a first interim opening pressure, determined for one series of inspiration pulses, for determining the pressures of the following series of inspiration pulses. For instance, in one delivered series of inspiration pulses having a pressure ramp from 10 to 30 cmH$_2$O, an interim opening pressure of 25 cmH$_2$O is determined. The next series of inspiration pulses could then have a pressure ramp from 22 to 35 cmH$_2$O.

In a further embodiment of the invention a blood gas analyzing unit is connected to a circulatory system of the subject for measuring the partial pressure of oxygen in the circulatory system (P$_a$O$_2$). The control unit then determines the optimal opening pressure based on the measured respiratory gas parameters and the measured P$_a$O$_2$. Basically, P$_a$O$_2$ should be above a certain threshold level when the lungs are sufficiently opened. Since there is a physiological response time for the circulatory system to react to changes in the state of the lungs, the same inspiration pulse should be supplied to the patient several times to allow for the circulatory system to respond.

When utilizing blood gas measurements for this purpose, it is advantageous first to determine an interim opening pressure according to the above and then to supply a series of ordinary square-shaped pressure pulses to the patient. The square-shaped pulse is utilized for increasing the efficient inspiration time for the opened lung. A pressure ramp, having a start pressure below the opening pressure and an end pressure above the opening pressure, would not open the lungs until the pressure reaches the opening pressure, and the lungs would only be open for the remainder of the inspiration pulse. In other words, the efficient inspiration time is shorter than the set inspiration time. Even though the lungs open eventually, the remaining efficient inspiration time could be insufficient for providing for a good gas exchange.

The peak pressure of these square-shaped pulses should be related to the determined interim opening pressure, e.g., of the same magnitude, 10% higher or similar. After one or a few minutes the circulatory system will have responded to improvements in gas exchange (if any) and the P$_a$O$_2$ can be measured. If the measured P$_a$O$_2$ exceeds the threshold, the lungs have been opened up sufficiently and the determined interim opening pressure is an optimal opening pressure. If the threshold is not reached, the interim opening pressure is not optimal, or the lungs are so damaged that the P$_a$O$_2$ can never reach the threshold. In the latter case, the previously described determination to obtain the optimal opening pressure is preferable. Care should also be taken to avoid over-distension and trauma.

The importance of P$_a$O$_2$ and a more general determination of an opening pressure based on measured P$_a$O$_2$ is disclosed in a simultaneously filed patent application entitled "Respiratory System for Determining an Opening Pressure of a Lung System and Maintaining the Lung System Open" having U.S. Ser. No. 08/651,608, filed May 22, 1996, having the same inventors and assignee as the present application.

In the present embodiment, the P$_a$O$_2$ is used to determine the optimal opening pressure either by selecting the first determined opening pressure at which the measured P$_a$O$_2$ exceeds a predetermined threshold as the optimal opening pressure or, if several interim opening pressures have been determined, the lowest interim opening pressure at which the measured P$_a$O$_2$ exceeds the predetermined threshold.

A method for determining an optimal opening pressure in a lung system includes the following steps.

At least one predetermined inspiration pulse is delivered to the lung system having an end pressure which is higher than the start pressure.

At least one respiratory gas parameter is measured.

An interim opening pressure is determined.

A partial pressure of oxygen in a blood sample from the subject circulatory system is measured.

The measured $P_aO_2$ is compared with predetermined threshold.

If the measured $P_aO_2$ is lower than the threshold, a new predetermined inspiration pulse, and the above steps are repeated.

If the measured $P_aO_2$ is higher than the threshold, the last determined interim opening pressure is selected as the optimal opening pressure.

The partial pressure of oxygen is used as a relevant prerequisite for determining when the lungs are sufficiently opened, i.e., a major part of the collapsed alveoli have been opened. The determined opening pressure for a specific inspiration pulse can be related to the resulting $P_aO_2$. An optimal opening pressure can then be defined as an opening pressure which results in a $P_aO_2$ which is higher than the predetermined threshold.

In a further version of the method the step of measuring at least one respiratory parameter includes the following steps.

The respiratory gas flow to the lung system is measured and the respiratory gas pressure in or near the lung system is measured. Additionally, the step of determining an interim opening pressure includes the following steps.

Inflection points or regions in the measured parameter respiratory gas flow are identified.

A latest identified inflection point or region is correlated to the measured parameter respiratory gas pressure.

The highest pressure related to the latest identified inflection point or region is determined as an interim opening pressure.

At least one inspiration pulse having a start pressure equal to or higher than the determined interim pressure is delivered to the lung system.

DESCRIPTION OF THE PREFERRED EMBODIMENTS

Figure 1:
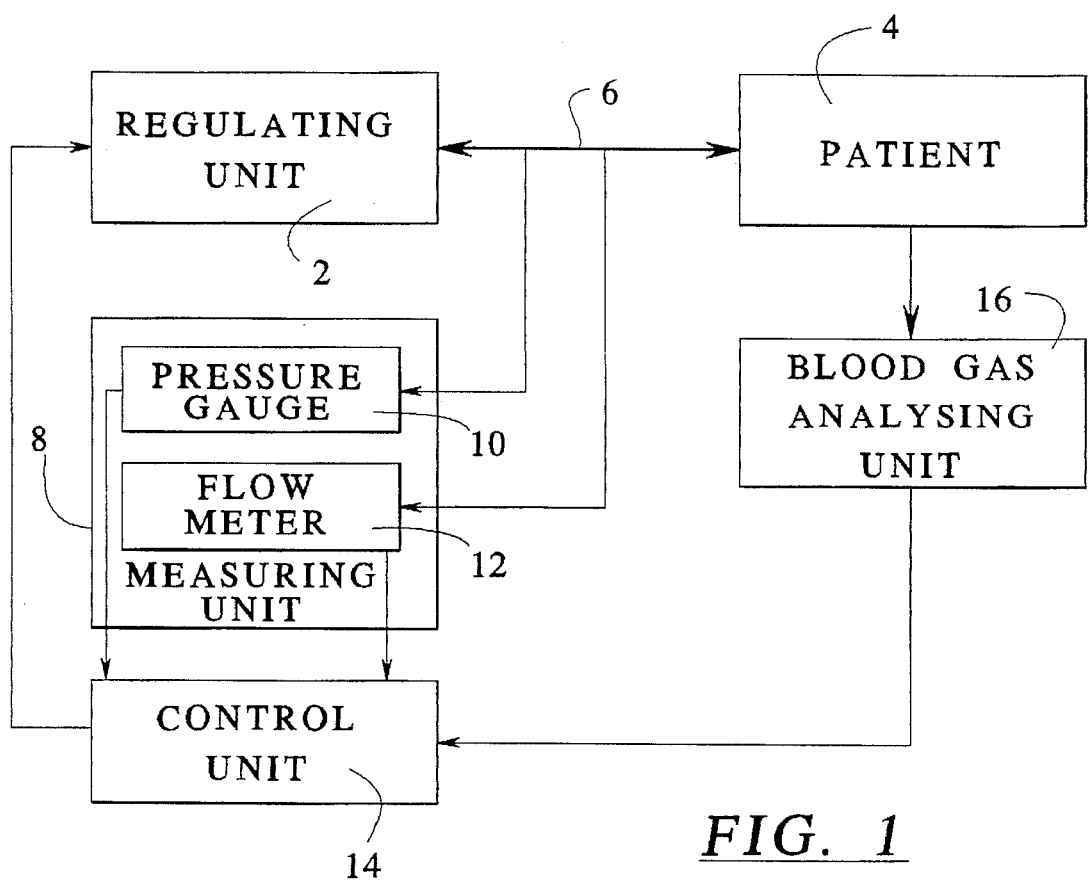
FIG. 1 schematically shows an arrangement according to the invention in a function block diagram.

The principal elements of the inventive arrangement are schematically shown in FIG. 1. It should be noted that the functional blocks do not necessarily represent separate physical apparatuses. A functional block may consist of several apparatuses and some of the functional blocks may be included within one apparatus. A regulating unit 2 is connected to a patient 4 via a gas delivery system 6. The regulating unit 2 can deliver a respiratory gas to the patient and remove exhaled gas from the patient 4. The regulating unit 2 could basically be a ventilator/respirator of any known construction, such as Servo Ventilator 300, Siemens-Elema AB, Sweden. A measuring unit 8 having a pressure gauge 10 and a flow meter 12 is connected to the gas delivery system 6 for measuring respiratory gas flow and pressure. The measured values are supplied to a control unit 14, which calculates an opening pressure based on the measured respiratory gas flow and pressure values. The control unit 14 can send signals to the regulating unit 2, e.g. when an optimal opening pressure has been found for delivering respiratory gas at that pressure and subsequently maintaining a pressure to keep the lungs open.

A blood gas analysing unit 16 is also connected to the patient 4 for measuring the partial pressure of oxygen ($P_aO_2$) in the blood of the patient's circulatory system. A blood gas analysing unit suitable for this kind of analysis is described in U.S. Pat. Nos. 4,841,974 and 5,225,063.

The interconnection between the blood gas analysing unit 16 and the circulatory system of the patient 4 can be made in several ways. For instance, a blood sample could be extracted from the blood system and analyzed in an analysing probe outside the patient, or a probe could be inserted into the circulatory system for in vivo measurement of the blood gas. Also, measurements can be made at varying time intervals. The measurement of $P_aO_2$ is made for obtaining an important parameter in the determining of an optimal opening pressure for the lungs of the patient.

Figure 2:
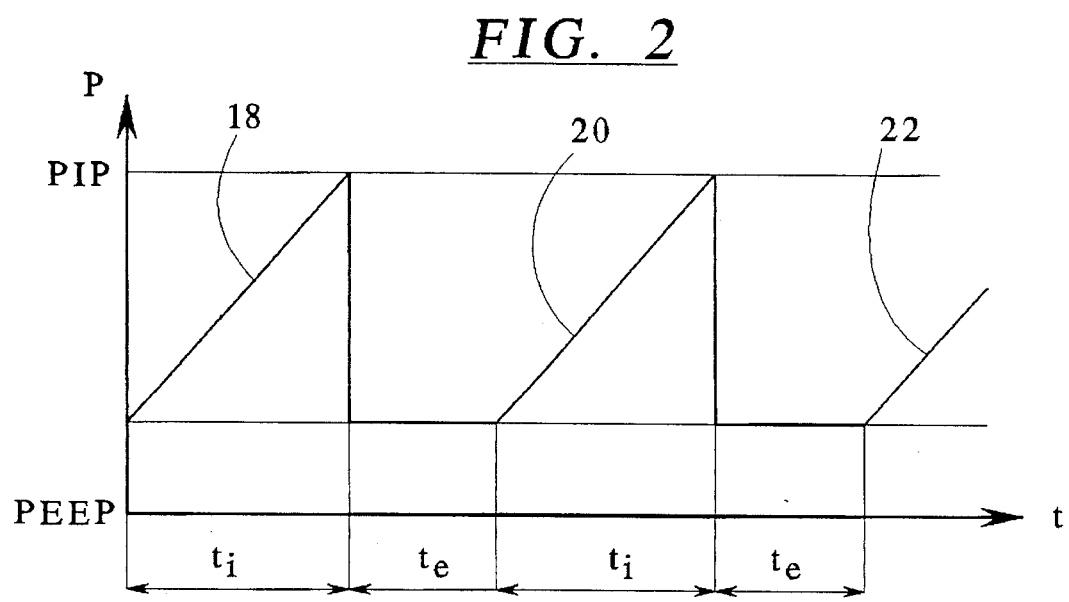
FIG. 2 illustrates a first inspiration pulse which can be delivered by the arrangement of FIG. 1 in order to determine an opening pressure.

The regulating unit 2 is adapted to deliver inspiration pulses of any shape regarding pressure. In other words, the regulating unit 2 can deliver inspiration pulses with a controlled pressure, which varies in a predetermined manner. For example, the regulating unit 2 can deliver inspiration pulses 18, 20 and 22 as shown in FIG. 2. Inspiration pulse 18 has a start pressure at PEEP level and an end pressure at PIP level. PEEP stands for Positive End Expiratory Pressure and is related to atmospheric pressure and can thus be any value larger than or equal to zero. Normally, PEEP is lower than 20 $cmH_2O$ when determining the optimal opening pressure. PIP stands for Peak Inspiratory Pressure and in relation to this application the PIP pressure is between 30 and 60 $cmH_2O$ for determining the optimal opening pressure. Both PEEP and PIP, however, could be selected from pressures outside the mentioned limits if necessary for opening a collapsed lung.

The inspiration pulse 18 has a duration of $t_i$, which is the inspiration-time. In connection with the present application, inspiration' times of 5 to 10 seconds are used. As with the pressures, however, shorter and longer inspiration times can be used when necessary. The inspiration time $t_i$ is followed by an expiration time $t_e$ and thereafter a second inspiration pulse 20 is delivered. As shown in FIG. 2 several identical inspiration pulses 18, 20 and 22 can be delivered in a sequence when determining the opening pressure. When delivering several identical inspiration pulses 18, 20 and 22, the measured respiratory gas flow is averaged. The calculated average flow is then utilized in determining the opening pressure.

Figure 4:
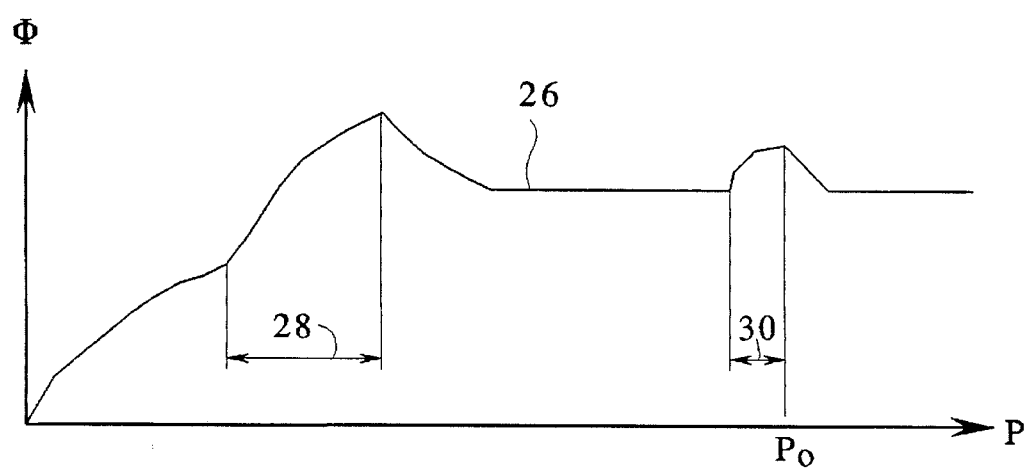
FIG. 4 shows a flow-pressure diagram illustrating how the opening pressure can be determined in the inventive method and apparatus.

The determination of the opening pressure is illustrated in FIG. 4, which is a diagram with a pressure-axis and a flow-axis. The curve 26 is measured flow in relation to measured pressure(or average flow in relation to pressure). In the curve 26, a first inflection region 28 can be identified where a sudden increase in flow has occurred. This inflection region represents the opening of a number of collapsed alveoli in the lung system of the patient 4. A second inflection region 30 can be identified at an even higher pressure. The second inflection region is much smaller than the first inflection region 28, but still represents the opening of some alveoli. Since it is preferable to open as much of the lung as possible, it is the upper pressure value of the second inflection region 30 that is selected as the opening pressure $P_O$.

After the opening pressure has been determined, several inspiration pulses having a start pressure equal to or higher than 35 the determined opening pressure are delivered to the patient. These pulses could be square-shaped and are delivered for testing whether the lungs will open sufficiently or not. The $P_aO_2$ is then measured and if the measured $P_aO_2$ does not exceed a predetermined threshold, the determined opening pressure P indicated in FIG. 4 is not high enough to achieve a sufficient opening of the lungs. A different inspiration pulse or series of inspiration pulses will then be delivered to the patient 4. The new inspiration pulse may, for instance, have a higher PEEP or a higher PIP (or both). These values can be selected based on the previously determined opening pressure.

The next inspiration pulse or pulses may also have another relation between inspiration time and expiration time. Varying inspiration times ti in relation to expiration times $t_e$ can be used to create intrinsic PEEP. Another respiration frequency can also be used for creating intrinsic PEEP. All these factors interact in different ways for different lungs and it is therefore not possible to have one specific inspiration pulse which will guarantee the opening of every collapsed lung.

A second series of inspiration pulses, e.g. having both a higher PEEP and a higher PIP, may result in a measured $P_aO_2$ which exceeds the predetermined threshold. The measured $P_aO_2$ then indicates that the lungs have opened up sufficiently and the determined opening pressure Po for that inspiration pulse is therefore the optimal opening pressure for this particular patient 4 at this particular time. Depending on the reason for the lung collapse of the constriction of the lungs, the individual response to the inspiration pulse may vary as the state of the lungs improves.

Another way of determining the optimal opening pressure is to deliver a sequence of inspiration pulses, all being different as to selected PEEP, PiP, $t_i$, $t_e$ or frequency. For all these inspiration pulses, an interim opening pressure is determined as shown in FIG. 4. A relation is then calculated based on the determined interim opening pressures and the supplied volume up to the determined interim opening pressure in each breath. In other words, the integral from zero to $P_0$ in the diagram of FIG. 4 for the curve 26 is calculated. In order to choose the optimal opening pressure, the quotient of interim opening pressure divided by calculated volume should be minimized. The minimization indicates that a large volume is delivered at a low pressure. It is also possible to use other mathematical relations between pressure and volume in order to obtain the optimal opening pressure. For example, the value of volume squared could be used in the quotient above, in order to increase the importance of supplying sufficient volumes at a low pressure.

Figure 3:
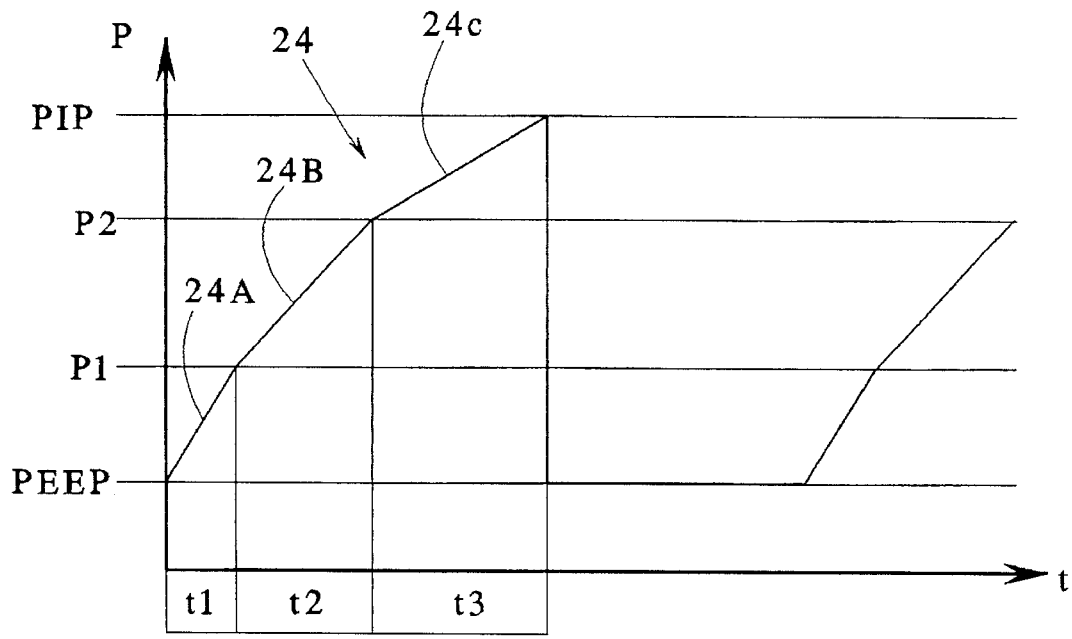
FIG. 3 illustrates a second inspiration pulse which can be delivered by the arrangement of FIG. 1 for determining the opening pressure.

FIG. 3 shows another kind of inspiration pulse 24, in which the increase in pressure is divided into several linear pressure stages, in this case three stages. A first pressure stage 24A elevates the pressure from the start pressure PEEP to pressure Pi at a time interval ti, a second pressure stage 24B elevates the pressure from Pi to P2 during time interval t2 and a bird pressure stage 24C elevates the pressure from P2 to PIP during the time interval t3. Pressure levels Pi and P2 are preferably selected so that the pressure P2 is slightly below a expected value for the optimal pressure or slightly below a previously determined interim opening pressure. The time intervals t1, t2 and t3 are preferably selected so that the third pressure stage 24C covers more than at least one third of the total inspiration $t_i$. Due to this structure of the inspiration pulse 24, the pressure increase during the third pressure stage 24C will be less steep than a ramp similar to the one in the inspiration pulse 18 in FIG. 2. By selecting P2 properly, the opening pressure will be situated in the third pressure stage 24C and the curve in the flow-pressure diagram will be more sensitive to minute changes in the flow.

Figure 5:
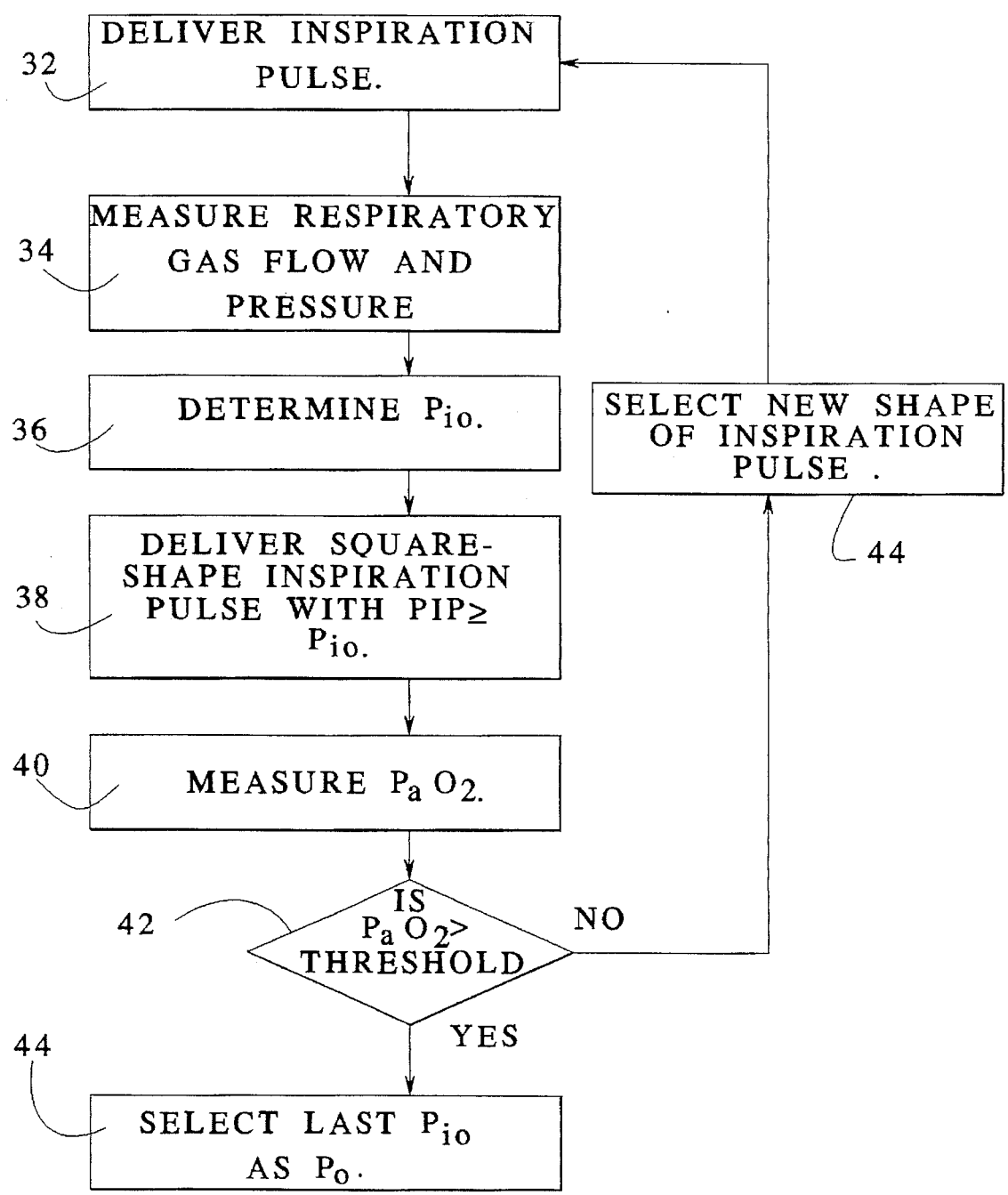
FIG. 5 shows a flow chart for a method of determining an optimal opening pressure in accordance with the invention.

FIG. 5 shows a flow chart for a method of determining an optimal opening pressure, which method can be carried out by the arrangement in FIG. 1. The flow chart only shows the necessary steps for obtaining the optimal opening pressure. According to the first block 32 an inspiration pulse is delivered to the patient. Respiratory gas flow and pressure are then measured, block 32. The steps described in blocks 32 and 34 can be repeated, if the same inspiration pulse is to be delivered several times, whereby average values for the measured respiratory gas flow are calculated. In the next step, block 36, an interim opening pressure is determined in the way shown in FIG. 4. A series of square-shaped inspiration pulses, having a PIP equal to or higher than the determined interim opening pressure is delivered, block 38. The $P_aO_2$ is then measured, block 40, and the measured value is compared with a predetermined threshold, block 42. If the measured $P_aO_2$ is lower than the threshold, output No in block 42, a new shape of the inspiration pulse is selected, block 46 the new inspiration pulse is then delivered as indicated in block 32 and the determining if an interim opening pressure and measurement of $P_aO_2$ is repeated.

If the measured $P_aO_2$ exceeds the threshold, output Yes in block 42, the last determined interim opening pressure is selected as the optimal opening pressure for the lung system, block 44.

If the measured $P_aO_2$ exceeds the threshold, output Yes in block 42, the last determined interim opening pressure is selected as the optimal opening pressure for the lung system, block 44.

Instead of measuring $P_aO_2$ for determining the optimum pressure, several different series of inspiration pulses can be delivered. For each series an interim opening pressure $P_{io}$, and the volume V supplied up to the interim opening pressure are determined and the quotient of these ($P_{io}/V$) is calculated and stored. After all series have been delivered the calculated quotients are compared and the $P_{io}$ for the least quotient is selected as the optimum opening pressure.

Although modifications and changes may be suggested by those skilled in the art, it is the intention of the inventors to embody within the patent warranted hereon all changes and modifications as reasonably and properly come within the scope of their contribution to the art.

We claim as our invention:

1. A respiratory apparatus comprising:
   regulating means for supplying a respiratory gas to the lung system of a patient;
   measuring means for measuring at least one respiratory gas parameter of said respiratory gas;
   control means for determining an optimal opening pressure of the lung system of the patient based on said at least one measured parameter; and
   said regulating means comprising means for delivering a predetermined inspiration pulse having an end pressure which is higher than said start pressure, and said measuring means comprising means for measuring said at least one respiratory gas parameter during delivery of said predetermined inspiration pulse.

2. A respiratory apparatus as claimed in claim 1 wherein said regulating means comprises means for controlling supply of respiratory gas to said lung system by increasing a respiratory gas pressure in linear stages from said start pressure to said end pressure.

3. A respiratory apparatus as claimed in claim 1 wherein said measuring means comprises a flow meter which measures a respiratory gas flow to said lung system, and wherein said control means comprises means for determining said optimum opening pressure based on slid respiratory gas flow.

4. A respiratory apparatus as claimed in claim 3 wherein said measuring means further comprises a pressure gauge for measuring a pressure of said respiratory gas substantially at said lung system, and wherein said control means comprises means for determining said optimal opening pressure based on said respiratory gas flow and said pressure.

5. A respiratory apparatus as claimed in claim 1 wherein said regulating means comprises means for delivering a series of consecutive, identical predetermined inspiration pulses, wherein said measuring means comprises means for measuring said at least one respiratory gas parameter during each of said inspiration pulses, and wherein said control means comprises means for calculating an average value of said measured parameters and wherein said means for determining the optimal opening pressure comprises means for determining the optimal opening pressure based on said average value.

6. A respiratory apparatus as claimed in claim 5 wherein said regulating means comprises means for delivering a sequence consisting of a plurality of said series, said predetermined inspiration pulses being identical in each series but differing from series-to-series, and wherein said control means comprises means for determining an interim opening pressure for each series and means for determining said optimal opening pressure based on all of the interim opening pressures.

7. A respiratory apparatus as claimed in claim 6 wherein said control means comprises means for identifying one of said series which achieves a predetermined relation between supplied gas volume an interim opening pressure and means for selecting the interim opening pressure of that series as said optimal opening pressure.

8. A respiratory apparatus as claimed in claim 1 further comprising:

blood gas an analyzing means interacting with the circulatory system of said patient, for measuring a partial pressure of oxygen of blood in said circulatory system and for emitting a partial pressure of oxygen measurement signal; and said control means comprising means supplied with said partial pressure of oxygen measurement signal for determining said optimal opening pressure based on said at least one respiratory gas parameter and said partial pressure of oxygen measurement signal.

9. A respiratory apparatus as claimed in claim 8 wherein said regulating means comprises means for delivering a series of said inspiration pulses, wherein said means for determining said optimal opening pressure comprises means for determining an interim opening pressure for each of said inspiration pulses, and means for identifying a first interim opening pressure at which said partial pressure of oxygen measurement value exceeds a predetermined threshold as said optimal opening pressure.

10. A respiratory apparatus as claimed in claim 8 wherein said regulating means comprises means for delivering a series of said inspiration pulses, wherein said means for determining said optimal opening pressure comprises means for determining an interim opening pressure for each of said inspiration pulses, and means for identifying a lowest interim opening pressure at which said partial pressure of oxygen measured value exceeds said predetermined threshold as said optimal opening pressure.

11. A method for determining an optimal opening pressure in a lung system of a subject, comprising the steps of:

(a) delivering an initial predetermined respiratory gas inspiration pulse to the lung system having an end pressure which is higher than a start pressure;

(b) measuring at least one respiratory gas parameter of said respiratory gas during delivery of said inspiration pulse;

(c) determining an interim opening pressure from said at least one respiratory gas parameter;

(d) measuring a partial pressure of oxygen in blood in the circulatory system of said subject to obtain a partial pressure of oxygen measured value;

(e) comparing said partial pressure of oxygen measured value to a predetermined threshold;

(f) if said partial pressure of oxygen measured value is lower than said threshold, selecting a new predetermined inspiration pulse different from said initial predetermined inspiration pulse, and repeating steps (a) through (e); and (g) if the partial pressure of oxygen measured value is higher than said threshold, selecting a latest interim opening pressure as the optimal opening pressure.

12. A method as claimed in claim 11, wherein step (b) comprises the steps of:

measuring a respiratory gas flow to said lung system; and measuring a respiratory gas pressure substantially at said lung system, and wherein step (c) comprises the steps of:

identifying inflection points in said respiratory gas flow;

correlating said inflection points to the respiratory gas pressure;

determining a highest pressure related to said inflection points as an interim opening pressure; and delivering a plurality of said inspiration pulses each having a start pressure equal to or greater than said interim opening pressure.

13. A method as claimed in claim 11, wherein step (b) comprises the steps of:

measuring a respiratory gas flow to said lung system; and measuring a respiratory gas pressure substantially at said lung system, and wherein step (c) comprises the steps of:

identifying inflection regions in said respiratory gas flow;

correlating said inflection regions to the respiratory gas pressure;

determining highest pressure related to said inflection regions as an interim opening pressure; and delivering a plurality of said inspiration pulses each having a start pressure equal to or greater than said interim opening pressure.

* * * * *